(12) United States Patent
Ooshima et al.

(10) Patent No.: US 12,042,572 B2
(45) Date of Patent: Jul. 23, 2024

(54) MEDICAL IMAGE DIAGNOSIS APPARATUS

(71) Applicant: CANON MEDICAL SYSTEMS CORPORATION, Otawara (JP)

(72) Inventors: Jun Ooshima, Nasushiobara (JP); Tomokazu Harada, Otawara (JP); Tatsuya Watanabe, Nasushiobara (JP); Akira Nishikori, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 324 days.

(21) Appl. No.: 17/455,251

(22) Filed: Nov. 17, 2021

(65) Prior Publication Data
US 2022/0160912 A1   May 26, 2022

(30) Foreign Application Priority Data

Nov. 20, 2020 (JP) .................................. 2020-193651
Sep. 30, 2021 (JP) .................................. 2021-161304

(51) Int. Cl.
*A61L 2/10* (2006.01)
*A61B 6/03* (2006.01)
*A61L 2/08* (2006.01)
*A61L 2/26* (2006.01)

(52) U.S. Cl.
CPC ................ *A61L 2/10* (2013.01); *A61B 6/032* (2013.01); *A61L 2/084* (2013.01); *A61L 2/26* (2013.01); *A61L 2202/11* (2013.01); *A61L 2202/121* (2013.01); *A61L 2202/14* (2013.01); *A61L 2202/24* (2013.01)

(58) Field of Classification Search
CPC ... A61L 2/10; A61L 2/084; A61L 2/26; A61L 2202/11; A61L 2202/121; A61L 2202/14; A61L 2202/24; A61B 6/032; A61B 6/4423
See application file for complete search history.

(56) References Cited

U.S. PATENT DOCUMENTS

2014/0294142 A1* 10/2014 Choi ...................... A61B 6/502
378/91

FOREIGN PATENT DOCUMENTS

JP         2005-176996 A      7/2005

* cited by examiner

*Primary Examiner* — Courtney D Thomas
(74) *Attorney, Agent, or Firm* — Oblon, McClelland, Maier & Neustadt, L.L.P.

(57) ABSTRACT

A medical image diagnosis apparatus according to one embodiment includes a gantry and a first light source. The gantry includes a first opening to which a subject is inserted. The first light source emits light capable of sterilization to the first opening.

12 Claims, 7 Drawing Sheets

MEDICAL IMAGE DIAGNOSIS APPARATUS

CROSS-REFERENCE TO RELATED APPLICATIONS

This application is based upon and claims the benefit of priority from Japanese Patent Application No. 2020-193651, filed on Nov. 20, 2020; the entire contents of which are incorporated herein by reference.

FIELD

Embodiments described herein relate to a medical image diagnosis apparatus.

BACKGROUND

One object to be achieved by the embodiments disclosed herein with reference to the drawings is to reduce the infection risk of people who are involved with the medical image diagnosis apparatus. The object to be achieved by the embodiments disclosed herein with reference to the drawings is, however, not limited to the aforementioned one. The object corresponding to each effect by each structure described in the embodiments below may be regarded as another object.

DETAILED DESCRIPTION

A medical image diagnosis apparatus according to an embodiment is hereinafter described in detail with reference to the attached drawings. Note that in the description below, the components denoted by the same reference symbol operate similarly and the overlapping description is omitted as appropriate.

First Embodiment

Figure 1:
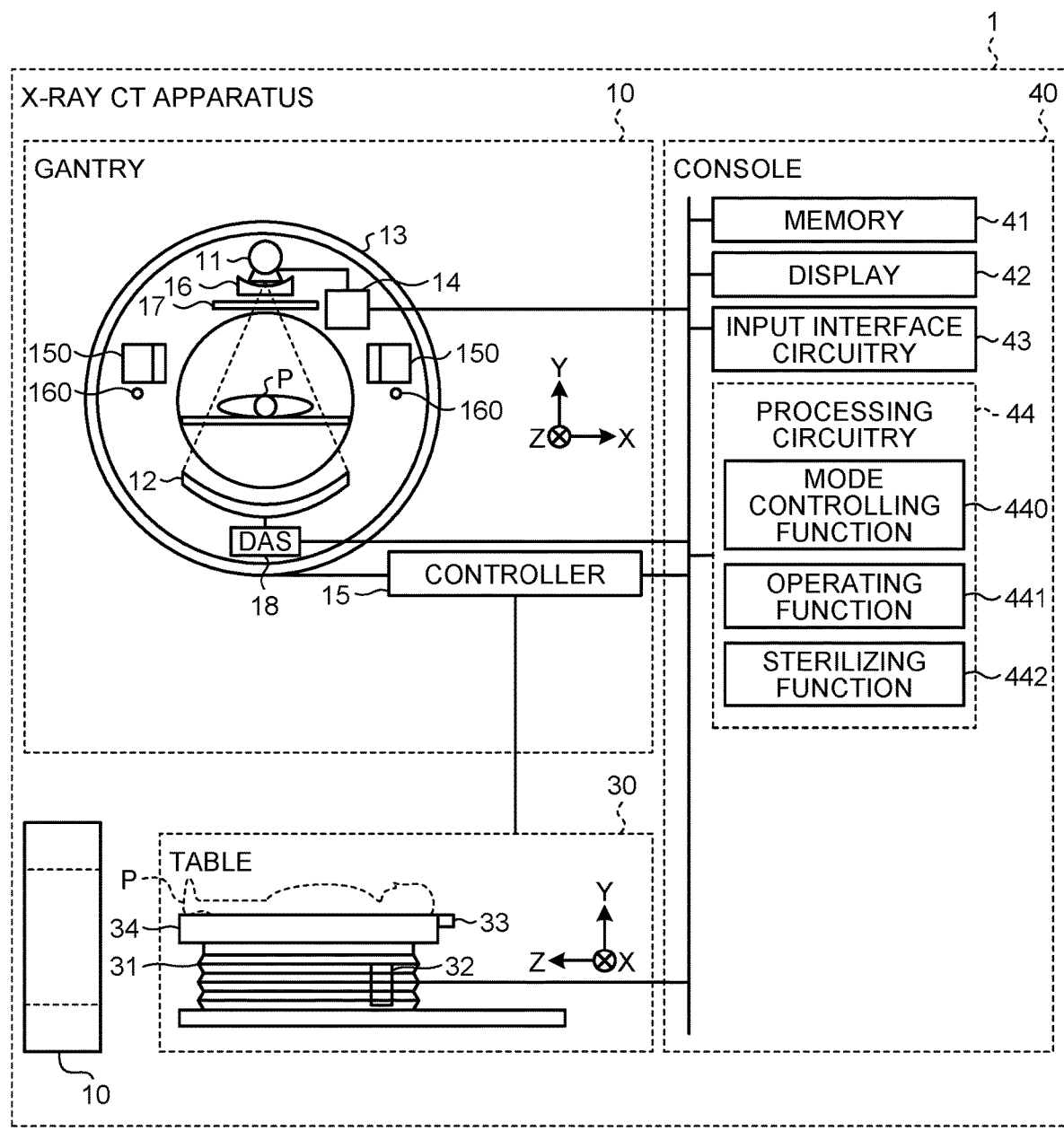
FIG. 1 is a block diagram illustrating one example of a structure of an X-ray CT apparatus 1 according to a first embodiment.

An X-ray computed tomography (CT) apparatus 1 is described as one example of a medical image diagnosis apparatus according to a first embodiment. FIG. 1 is a block diagram illustrating one example of a structure of the X-ray CT apparatus 1 according to the first embodiment. As illustrated in FIG. 1, the X-ray CT apparatus 1 according to the present embodiment includes a gantry 10, a table 30, and a console 40.

The gantry 10 and the table 30 are installed in an inspection room, for example. In a case of photographing a subject P, the gantry 10 delivers X-rays. In this case, the gantry 10 needs to prevent medical workers including a radiologist who operates the gantry 10 from being exposed. In view of this, the console 40 is installed in a console room adjacent to the inspection room, for example.

In FIG. 1, a rotation axis of a rotation frame 13 in a non-tilted state or a longitudinal direction of a tabletop 33 of the table 30 is a Z-axis direction. In addition, an axial direction that is orthogonal to the Z-axis direction and horizontal to a floor surface is an X-axis direction. In addition, an axial direction that is orthogonal to the Z-axis direction and perpendicular to the floor surface is a Y-axis direction. In FIG. 1, the gantry 10 is drawn from a plurality of directions for clarification, and the X-ray CT apparatus 1 includes one gantry 10.

The gantry 10 is an apparatus as a photographing system for scanning the subject P with X-rays. The gantry 10 includes a tubular opening part 110 to which the subject P is inserted. Moreover, the gantry 10 includes an X-ray tube 11, a wedge 16, a collimator 17, an X-ray detector 12, an X-ray high-voltage circuitry 14, a data acquisition system (DAS) 18, the rotation frame 13, a controller 15, operation panels 150, operation buttons 160, and the table 30.

The X-ray tube 11 is a vacuum tube through which thermo electrons are delivered from a negative pole (filament) to a positive pole (target) by application of high voltage from the X-ray high-voltage circuitry 14.

The wedge 16 is a filter to adjust the X-ray quantity of the X-rays delivered from the X-ray tube 11. Specifically, the wedge 16 is a filter that transmits and attenuates the X-rays delivered from the X-ray tube 11 so that the X-rays delivered from the X-ray tube 11 to the subject P has a predetermined distribution.

The wedge 16 is a wedge filter or a bow-tie filter, for example, and formed by processing aluminum so as to have a predetermined target angle or predetermined thickness.

The collimator 17 is a lead plate or the like for narrowing the irradiation range of the X-rays transmitting through the wedge 16, and a slit is formed by combining a plurality of lead plates or the like.

The X-ray detector 12 detects the X-rays delivered from the X-ray tube 11. More specifically, the X-ray detector 12 detects the X-rays delivered from the X-ray tube 11 and transmitting through the subject P, and outputs an electric signal corresponding to the X-ray quantity to a data acquisition device (DAS 18). The X-ray detector 12 includes, for example, a plurality of X-ray detection element columns in which a plurality of X-ray detection elements are arranged in a channel direction along one arc using a focal point of the X-ray tube 11 as a center. The X-ray detector 12 has a structure in which, for example, the X-ray detection element columns where the X-ray detection elements are arranged in the channel direction are arranged in a slice direction (also referred to as body axis direction or column direction).

The X-ray detector 12 is an indirect conversion type detector including a grid, a scintillator array, and an optical sensor array, for example. The scintillator array includes a plurality of scintillators and the scintillator includes scintillator crystal that outputs light with the photon quantity corresponding to the incident X-ray quantity. The grid includes an X-ray blocking plate that is disposed on a surface of the scintillator array on the X-ray incidence side and has a function of absorbing scattering X-rays. The optical sensor array has a function of converting into an electric signal corresponding to the light quantity from the scintillator, and includes an optical sensor such as a photomultiplier tube (PMT). Note that the X-ray detector 12 may be a direct conversion type detector including a semiconductor element for converting the incident X-rays into the electric signal.

The X-ray high-voltage circuitry 14 includes a high-voltage generating circuitry including electric circuits such as a transformer (trans) and a rectifier and having a function of generating high voltage to be applied to the X-ray tube 11, and an X-ray control controller that controls the output voltage according to the X-rays delivered from the X-ray tube 11. The high-voltage generating circuitry may employ a transformer type or an inverter type. Note that the X-ray high-voltage circuitry 14 may be provided to either the rotation frame 13 or a fixed frame (not illustrated) side of the gantry 10. The fixed frame is a frame that supports the rotation frame 13 rotatably.

The DAS 18 includes an amplifier that amplifies the electric signal output from each X-ray detection element in the X-ray detector 12 and an A/D converter that converts the electric signal into a digital signal, and generates detection data. The detection data generated by the DAS 18 is transferred to the console 40.

The rotation frame 13 is an annular frame that supports the X-ray tube 11 and the X-ray detector 12 so that they face each other, and rotates the X-ray tube 11 and the X-ray detector 12 by the controller 15. Note that the rotation frame 13 may further support the X-ray high-voltage circuitry 14 or the DAS 18 in addition to the X-ray tube 11 and the X-ray detector 12. Note that, for example, the detection data acquired by the DAS 18 is transmitted from a transmitter 21 including a light-emitting diode provided to the rotation frame 13 to a receiver 22 including a photodiode provided to a non-rotation part of the gantry 10 such as a fixed frame by optical communication and then transferred to the console 40. Note that how the detection data is transmitted from the rotation frame 13 to the non-rotation part of the gantry 10 is not limited to the optical communication and may be another noncontact data transmission method.

The controller 15 includes a processing circuit including a CPU or the like, and a driving mechanism such as a motor or an actuator. The controller 15 has a function of controlling the operation of the gantry 10 and the table 30 upon the reception of an input signal from an input interface circuitry 43 attached to the console 40 or an input interface attached to the gantry 10. Moreover, upon the reception of the input signal, the controller 15 controls to rotate the rotation frame 13 or operate the gantry 10 and the table 30.

For example, the controller 15 tilts the gantry 10 in a manner that the controller 15 rotates the rotation frame 13 using an axis parallel to the X-axis direction as a center, on the basis of information about the inclination angle (tilt angle) input by the input interface attached to the gantry 10.

The operation panel 150 includes a touch panel display, for example. More specifically, when a displayed image is touched, the operation panel 150 receives the operation according to the touched image.

The operation button 160 is a button to receive the operation.

The table 30 is an apparatus on which the subject P to be scanned is placed and by which the subject P is moved, and includes a base 31, a table drive circuitry 32, the tabletop 33, and a supporting part 34. The base 31 is a housing that supports the supporting part 34 in a manner that the supporting part 34 is movable in a vertical direction. The table drive circuitry 32 is an actuator or a motor that moves the tabletop 33 on which the subject P is placed, in a longitudinal direction thereof (Z-axis direction in FIG. 1). The tabletop 33 provided on an upper surface of the supporting part 34 is a plate on which the subject P is placed. That is to say, the table 30 includes the tabletop 33 on which the subject P is placed. The table drive circuitry 32 may move the supporting part 34 in the longitudinal direction of the tabletop 33 in addition to the tabletop 33.

The table drive circuitry 32 moves the base 31 vertically in accordance with a control signal from the controller 15. The table drive circuitry 32 moves the tabletop 33 in the longitudinal direction in accordance with the control signal from the controller 15.

The console 40 receives the user's operation from the X-ray CT apparatus 1 and reconfigures the X-ray CT image data from the detection data collected by the gantry 10. The console 40 includes a memory 41, a display 42, the input interface circuitry 43, and a processing circuitry 44.

The memory 41 is achieved by, for example, a semiconductor memory element such as a random access memory (RAM) or a flash memory, a hard disk, an optical disk, or the like. The memory 41 stores projection data and reconfiguration image data therein, for example.

The memory 41 stores dedicated computer programs for achieving a mode controlling function 440, an operating function 441, and a sterilizing function 442 that are described below.

The display 42 is a monitor that the user sees, and displays various kinds of information. For example, the display 42 outputs a medical image (CT image) generated by the processing circuitry 44, a graphical user interface (GUI) to receive various kinds of operation from the user, and the like. For example, the display 42 is a liquid crystal display or a cathode ray tube (CRT) display.

The input interface circuitry 43 receives various kinds of input operation from the user, converts the received input operation into the electric signal, and outputs the electric signal to the processing circuitry 44. For example, the input interface circuitry 43 receives a collecting condition when the projection data is collected, a reconfiguring condition when the CT image is reconfigured, an image processing condition when a post-processed image is generated from the CT image, and the like from the user. In another example, the input interface circuitry 43 is achieved by a mouse, a keyboard, a trackball, a switch, a button, a joystick, or the like.

The processing circuitry 44 controls the entire operation of the X-ray CT apparatus 1. The processing circuitry 44 includes, for example, the mode controlling function 440, the operating function 441, and the sterilizing function 442. In the embodiment, the respective processing functions performed by the mode controlling function 440, the operating function 441, and the sterilizing function 442 corresponding to the structure components are stored in the memory 41 as computer-executable computer programs. The processing circuitry 44 is a processor that reads out the computer program from the memory 41 and executes the computer program so as to achieve the function corresponding to the computer program. In other words, the processing circuitry 44 having read out the computer program has the corresponding function illustrated in the processing circuitry 44 in FIG. 1.

In FIG. 1, the mode controlling function 440, the operating function 441, and the sterilizing function 442 are achieved by one processor; however, the processing circuitry 44 may be formed by a combination of a plurality of independent processors and each processor may execute the computer program to achieve the function. In FIG. 1, one storage circuit such as the memory 41 stores the computer program corresponding to each processing function; however, a plurality of storage circuits may be dispersedly disposed and the processing circuitry 44 may read out the corresponding computer program from the individual storage circuit.

The term "processor" used in the above description refers to a circuit such as a central processing unit (CPU), a graphical processing unit (GPU), an application specific integrated circuit (ASIC), or a programmable logic device (for example, a simple programmable logic device (SPLD), a complex programmable logic device (CPLD), or a field programmable gate array (FPGA)). The processor achieves the function by reading out and executing the computer program saved in the memory 41. The computer program, instead of being saved in the memory 41, may be directly incorporated in the circuit of the processor. In this case, the processor achieves the function by reading out and executing the computer program incorporated in the circuit.

The functions of the processing circuitry 44 are described below.

Figure 2:
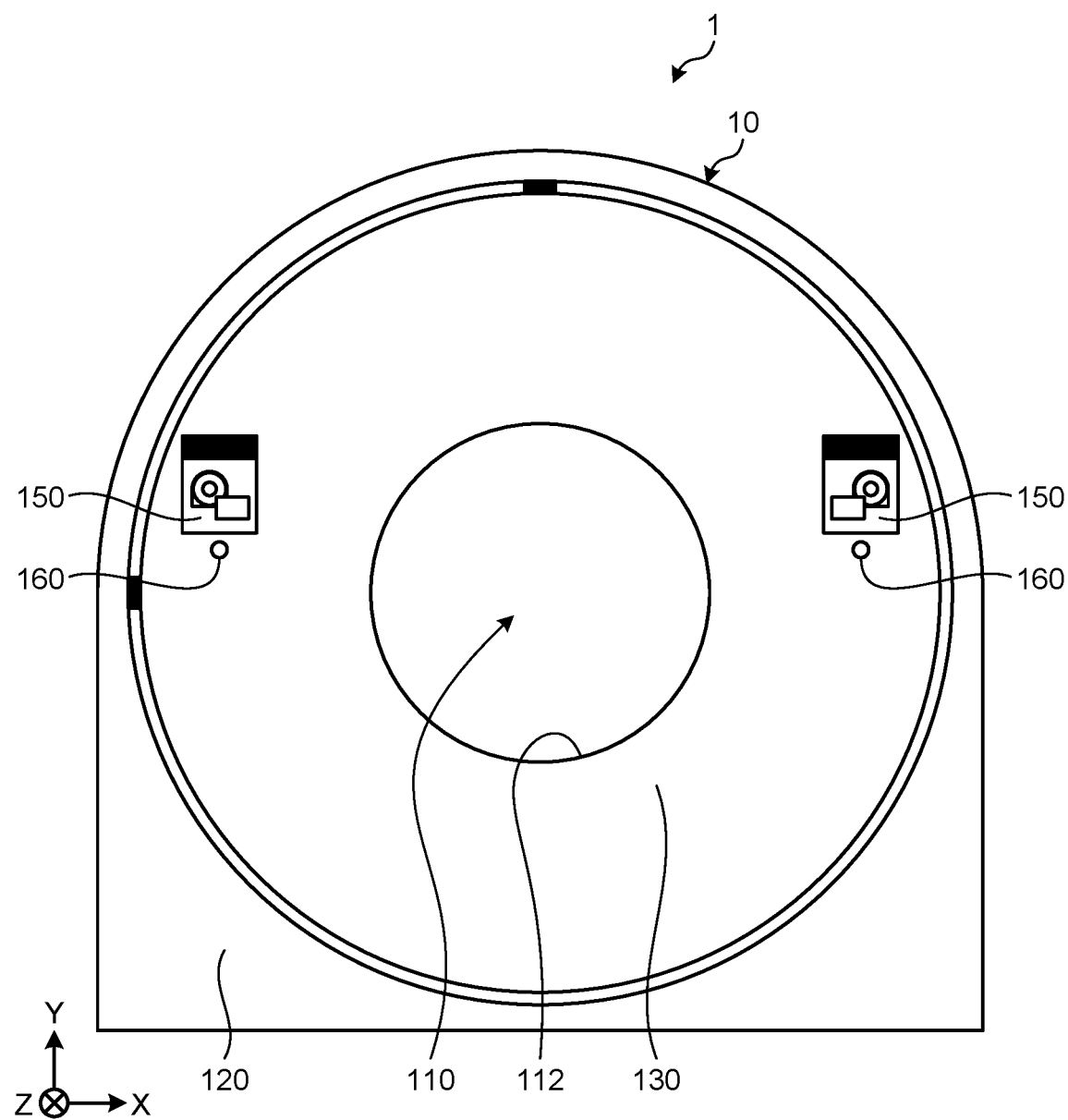
FIG. 2 is a front view illustrating one example of the external appearance of a gantry of the X-ray CT apparatus according to the first embodiment.
Figure 3:
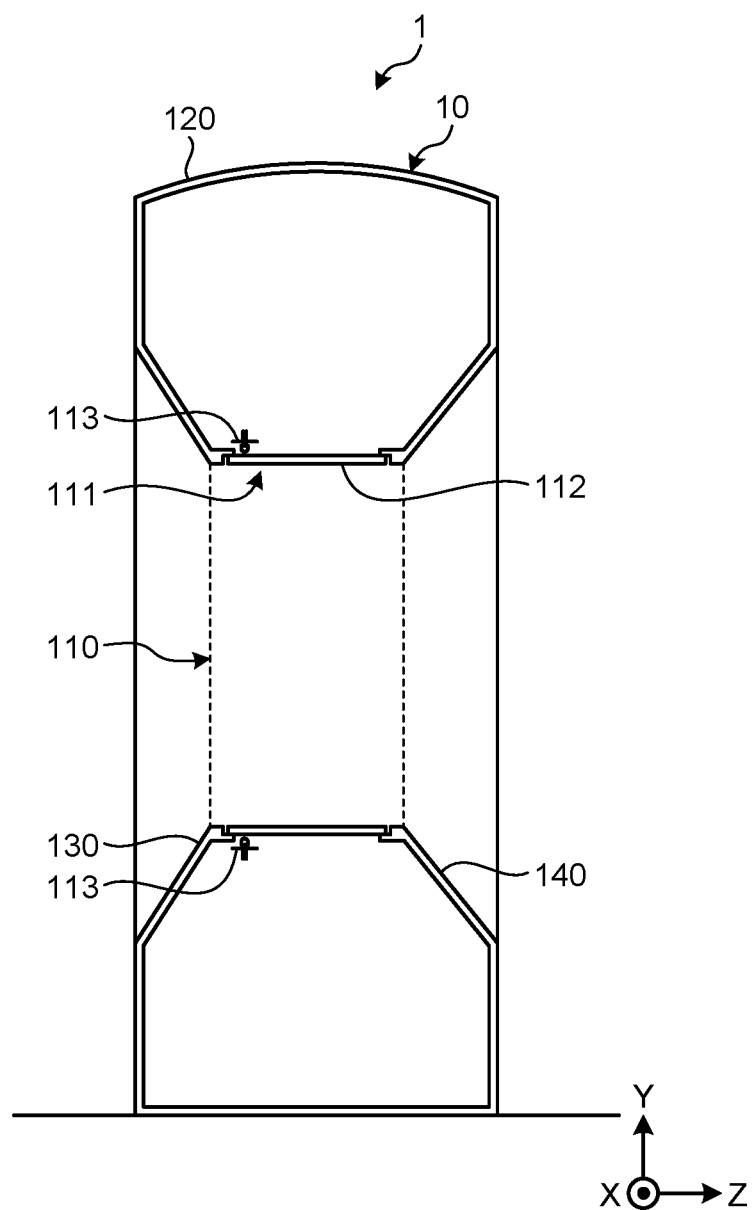
FIG. 3 is a cross-sectional view illustrating one example of the gantry of the X-ray CT apparatus according to the first embodiment.

Next, the external appearance of the X-ray CT apparatus 1 according to the first embodiment is described. FIG. 2 is a front view illustrating one example of the external appearance of the gantry 10 of the X-ray CT apparatus 1 according to the first embodiment. FIG. 3 is a cross-sectional view illustrating one example of the gantry 10 of the X-ray CT apparatus 1 according to the first embodiment.

The gantry 10 is an apparatus that irradiates the subject P such as a patient with X-rays and collects the projection data from the detection data obtained by detecting the X-rays transmitting through the subject P. The gantry 10 is covered with an exterior cover 120. The gantry 10 includes the opening part 110 to which the subject P is inserted. The opening part 110 is one example of a first opening. The opening part 110 is an opening provided at a substantial center of the gantry 10 and formed to have a tubular shape to which the subject P is inserted. To the opening part 110, the subject P placed on the tabletop 33 (see FIG. 6) of the table 30 (see FIG. 6) is inserted. The opening part 110 is provided in a photographing region formed near the rotation axis of the X-ray tube 11 and the X-ray detector 12.

A front side of the gantry 10 includes a first flare part 130 with a shape recessed toward the opening part 110. The front side corresponds to the side of the gantry 10 where the table 30 is disposed. Similarly, a rear side of the gantry 10 includes a second flare part 140 with a shape recessed toward the opening part 110. The rear side corresponds to the side opposite to the front side, where the table 30 is not disposed in the gantry 10.

The exterior cover 120 is not provided to a surface of the gantry 10 that is in contact with the opening part 110, and an internal opening 111 that releases the inside of the gantry 10 is provided. The internal opening 111 is closed by a closing cover 112 formed to have a tubular shape. That is to say, the gantry 10 includes the closing cover 112 that covers the internal opening 111 provided to the surface in contact with the opening part 110. The internal opening 111 is one example of a second opening.

The closing cover 112 is a cover with a thickness of 3 to 4 mm. The closing cover 112 is formed of a material that can transmit X-rays. The X-rays delivered from the X-ray tube 11 passes ⅓ of a substantially central region of the closing cover 112 in the Z-axis direction. In addition, the closing cover 112 is colored so that the X-ray tube 11 or the X-ray detector 12 in the gantry 10 is not seen by the subject P inserted into the opening part 110. Moreover, the closing cover 112 is formed of a material that can transmit ultraviolet rays, such as plastic. Note that a first sterilizing light source 113 illustrated in FIG. 3 is disposed inside the closing cover 112. However, the first sterilizing light source 113 may be disposed not inside but outside the closing cover 112.

The first sterilizing light source 113 is disposed outside an X-ray passing region from the X-ray tube 11 to the X-ray detector 12. More specifically, the first sterilizing light source 113 is disposed along a front edge of the closing cover 112 on the inside of the exterior cover 120. That is to say, the first sterilizing light source 113 is disposed inside the closing cover 112 and on the side where the table 30 on which the subject P is placed exists.

The first sterilizing light source 113 is a light source that emits the light capable of sterilization. Sterilization means to reduce the number of viruses, bacteria, or other microorganisms. Moreover, sterilization can be replaced by antisepsis, bacteria killing, bacteria elimination, or disinfection. The term bacteria killing refers to deaden (deactivate) bacteria, viruses, or other microorganisms existing in the object. That is to say, the first sterilizing light source 113 is a light source of light that can reduce the number of viruses, bacteria, and the like. For example, the first sterilizing light source 113 is a light source that emits ultraviolet rays.

The first sterilizing light source 113 is disposed inside the gantry 10 with respect to the closing cover 112 and faces the opening part 110. That is to say, the first sterilizing light source 113 emits the light capable of sterilization to the center of the opening part 110. The first sterilizing light source 113 is one example of a first light source. The closing cover 112 is formed of a material that transmits ultraviolet rays.

In the case of regarding the rotation axis of the X-ray tube 11 and the X-ray detector 12 as a center, the first sterilizing light source 113 is disposed 360 degrees along the circumference around the rotation axis. Note that the first sterilizing light source 113 may be disposed along the entire circumference (360 degrees) as described above; however, the embodiment of the present invention is not limited to this example. For example, the first sterilizing light source 113 may be absent by about several centimeters or ten and several centimeters in the circumferential direction. Alternatively, the first sterilizing light source 113 may be disposed at intervals instead of being disposed entirely 360 degrees along the circumference around the rotation axis. For example, the first sterilizing light source 113 may be disposed at intervals of 10 cm. Further alternatively, the first sterilizing light source 113 may be disposed at a part of the circumference 360 degrees around the rotation axis. For example, the first sterilizing light source 113 may be disposed at a 180-degree part on the upper side or at a 270-degree part on the upper side out of the circumference 360 degrees around the rotation axis. The first sterilizing light source 113 may irradiate the space of the opening part 110 or the first flare part 130 with sterilizing light through the closing cover 112. Thus, the first sterilizing light source 113 can sterilize the first flare part 130 even if the first flare part 130 is contaminated with the subject P's vomit, a contrast medium, or the like.

When the tabletop 33 of the table 30 (see FIG. 6) is inserted into the opening part 110, the first sterilizing light source 113 irradiates the tabletop 33 with the sterilizing light. Thus, the first sterilizing light source 113 can sterilize the tabletop 33. Note that the gantry 10 in FIG. 3 includes one first sterilizing light source 113. However, typically, the gantry 10 includes a plurality of the first sterilizing light sources 113. The first sterilizing light source 113 in FIG. 3 is disposed on the front side where the table 30 is disposed; however, the first sterilizing light source 113 may be disposed on the rear side opposite to the front side.

As illustrated in FIG. 2, the gantry 10 includes the operation panel 150 to receive the touch operation on each of left and right sides of the opening part 110. The operation panel 150, when the displayed image is touched, receives the operation according to the touched image.

The gantry 10 includes the operation button 160 below the operation panel 150. The operation button 160 is a button to receive the operation associated with the operation button 160. Note that the gantry 10 in FIG. 2 includes one operation button 160 below each operation panel 150. However, the gantry 10 may include more than one operation button 160 below the operation panel 150.

The operation panel 150 and the operation button 160 receive various kinds of operation. That is to say, the operation panel 150 and the operation button 160 are touched by medical staffs. Therefore, the medical staffs have risks of being infected with the infectious disease through the operation panel 150 and the operation button 160. In view of this, it is necessary to reduce the risk of infection of the medical staff with the infectious disease. For this purpose, the operation panel 150 and the operation button 160 are sterilized.

Next, sterilizing mechanisms of the operation panel 150 and the operation button 160 are described.

Figure 4:
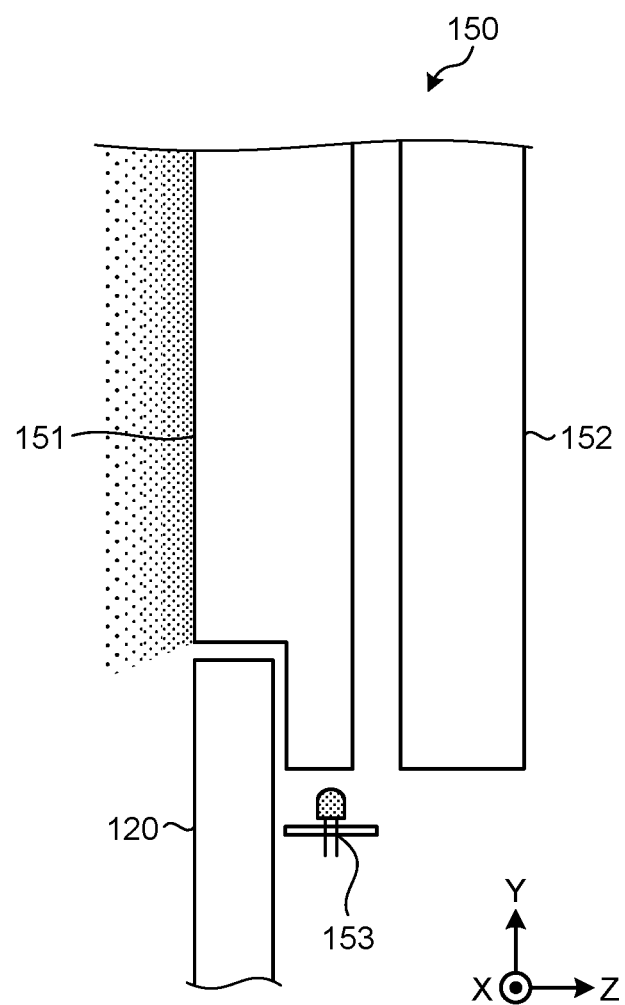
FIG. 4 is a cross-sectional view illustrating one example of a sterilizing structure of an operation panel of the X-ray CT apparatus according to the first embodiment.

FIG. 4 is a cross-sectional view illustrating one example of the sterilizing structure of the operation panel 150 of the X-ray CT apparatus 1 according to the first embodiment. The operation panel 150 receives the touch operation. The operation panel 150 releases light capable of sterilization.

More specifically, the operation panel 150 is surrounded by the exterior cover 120. The operation panel 150 includes a panel cover 151 that can transmit visible light. The panel cover 151 is formed of a member that transmits ultraviolet rays. The operation panel 150 includes a touch panel display 152 inside the panel cover 151. The touch panel display 152 displays various kinds of images and receives the touch operation through the panel cover 151.

The operation panel 150 includes a second sterilizing light source 153 that irradiates the panel cover 151 with light capable of sterilization inside the exterior cover 120 covering the gantry 10. The second sterilizing light source 153 is one example of a second light source. For example, the second sterilizing light source 153 is a light source that emits ultraviolet rays. The operation panel 150 in FIG. 4 includes the second sterilizing light source 153 below the panel cover 151. However, typically, the second sterilizing light source 153 is disposed along the peripheral four sides of the panel cover 151. Instead of having the second sterilizing light source 153 along all the peripheral four sides of the panel cover 151, the operation panel 150 may have the second sterilizing light source 153 along a part of the four sides. The second sterilizing light source 153 irradiates the panel cover 151 with the light capable of sterilization. The light emitted from the second sterilizing light source 153 propagates through the panel cover 151 and is released from the surface of the panel cover 151 to the outside of the operation panel 150. That is to say, the operation panel 150 releases the light capable of sterilization propagating through the panel cover 151. Thus, the surface of the operation panel 150 is sterilized with the light emitted from the second sterilizing light source 153.

The gantry 10 in FIG. 4 includes the two operation panels 150. However, the gantry 10 may exclude the operation panel 150 or may include one operation panel 150 or three or more operation panels 150. The position of the operation panel 150 in the gantry 10 in FIG. 4 is just one example and may be an arbitrary position.

Figure 5:
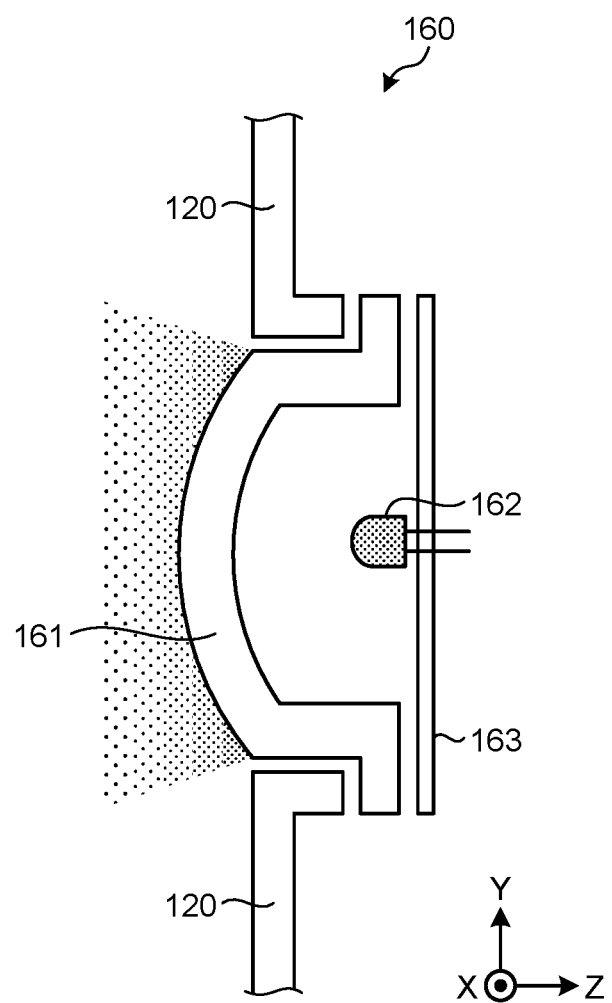
FIG. 5 is a cross-sectional view illustrating one example of a sterilizing structure of an operation button of the X-ray CT apparatus according to the first embodiment.

FIG. 5 is a cross-sectional view illustrating one example of the sterilizing structure of the operation button 160 of the X-ray CT apparatus 1 according to the first embodiment. The gantry 10 includes the operation button 160 that receives the operation. The operation button 160 releases light capable of sterilization.

The operation button 160 is surrounded by the exterior cover 120. Moreover, the operation button 160 has its front surface covered with a button cover 161. The operation button 160 includes a third sterilizing light source 162 that emits light capable of sterilization inside the button cover 161 that can transmit visible light. The button cover 161 is formed of a member that transmits visible light and ultraviolet rays. The operation button 160 includes a pedestal 163 where the third sterilizing light source 162 is disposed inside the button cover 161. The button cover 161 has its outer edge in contact with the pedestal 163. When the operation button 160 is pressed down, the button cover 161 presses down the pedestal 163. The pedestal 163 conveys a switch below the pedestal 163 that the pedestal 163 is pressed down. Thus, the operation button 160 receives the operation by the pressing.

The button cover 161 is formed of a member that transmits visible light and ultraviolet rays. The third sterilizing light source 162 is a light source that emits light capable of sterilization. For example, the third sterilizing light source 162 is a light source that emits ultraviolet rays. The third sterilizing light source 162 delivers light to the outside of the button cover 161 through the button cover 161. Thus, the surface of the operation button 160 is sterilized by the light emitted from the third sterilizing light source 162.

Note that the operation button 160 in FIG. 5 includes one third sterilizing light source 162. However, the operation button 160 may include not just one but a plurality of the third sterilizing light sources 162.

The gantry 10 in FIG. 2 includes the two operation buttons 160. However, the gantry 10 may exclude the operation button 160 or include one operation button 160 or three or more operation buttons 160. Furthermore, the arrangement position of the operation button 160 in the gantry 10 in FIG. 2 is one example, and may be arbitrarily determined.

Figure 6:
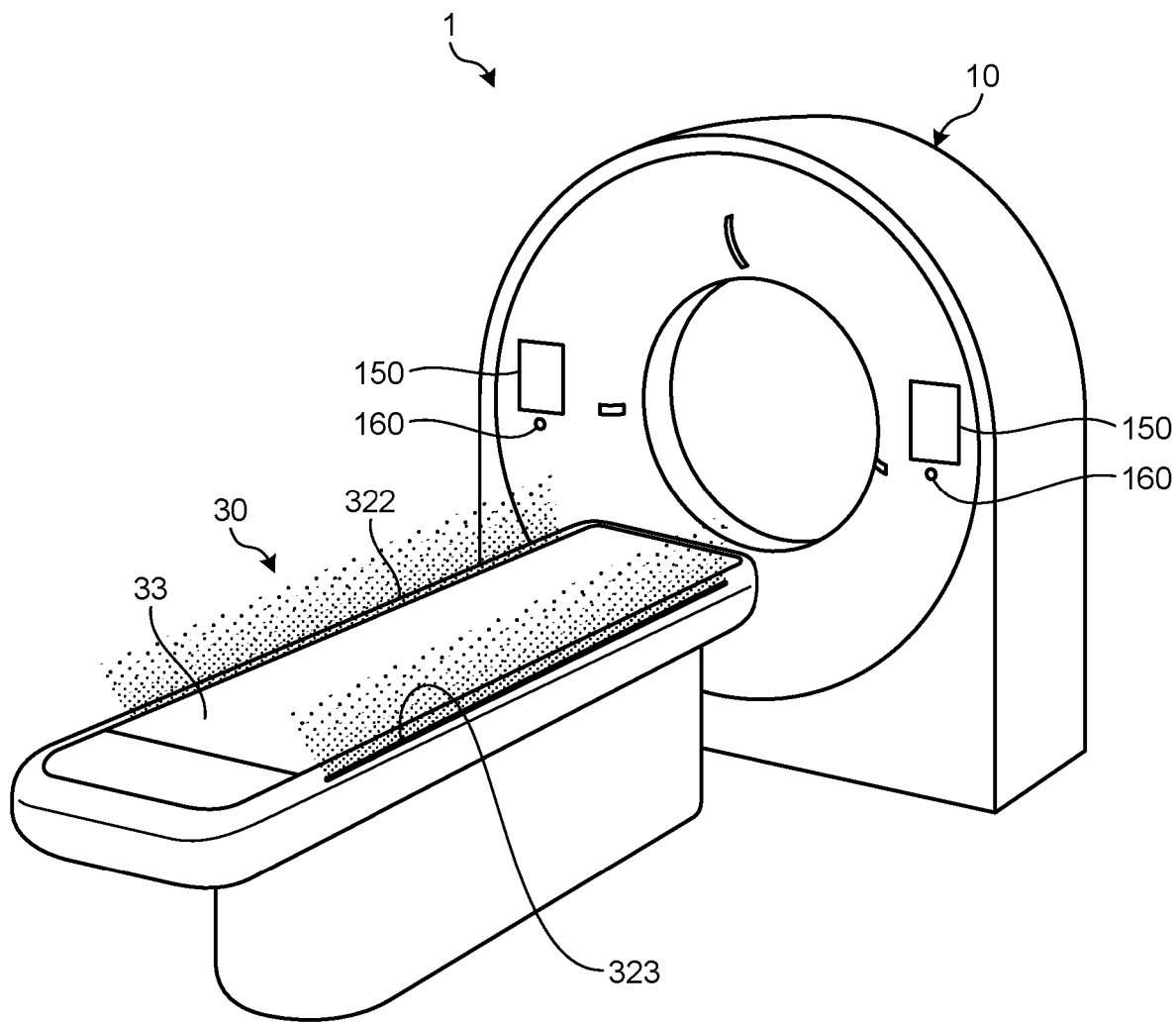
FIG. 6 is a cross-sectional view illustrating one example of a sterilizing structure of a table of the X-ray CT apparatus according to the first embodiment.

Next, the table 30 on which the subject P such as a patient is placed (see FIG. 6) is described. FIG. 6 is a cross-sectional view illustrating one example of a sterilizing structure of the table 30 of the X-ray CT apparatus 1 according to the first embodiment.

The X-ray CT apparatus 1 includes the table 30. The table 30 includes the tabletop 33 on which the subject P such as a patient is placed. Therefore, the subject P is exposed to the risk of being infected with the infectious disease through the tabletop 33 of the table 30. Accordingly, it is necessary to reduce the risk of infection of the medical staff or the patient with the infectious disease. In view of this, the table 30 performs the sterilization. That is to say, the tabletop 33 includes a fourth sterilizing light source that emits light capable of sterilization. For example, the fourth sterilizing light source is a light source emitting ultraviolet rays. The fourth sterilizing light source is one example of a fourth light source.

More specifically, on the tabletop 33, a first sterilizing part 322 and a second sterilizing part 323 are arranged along an edge substantially parallel to the longitudinal direction of the tabletop 33. The first sterilizing part 322 and the second sterilizing part 323 are disposed as the fourth sterilizing light source emitting the light capable of sterilization inside a protective cover that can transmit visible light and ultraviolet rays. That is to say, the fourth sterilizing light source is disposed along the edge of the tabletop 33 in the longitudinal direction. The fourth sterilizing light source faces upward and is aligned along the edge substantially parallel to the longitudinal direction of the tabletop 33. Therefore, the first sterilizing part 322 and the second sterilizing part 323 can sterilize the upper surface of the tabletop 33. Moreover, the first sterilizing part 322 and the second sterilizing part 323, when inserted into the gantry 10, can sterilize the opening part 110 by emitting the light capable of sterilization.

Note that the table 30 in FIG. 6 includes the first sterilizing part 322 and the second sterilizing part 323. However, the table 30 may include one of the first sterilizing part 322 and the second sterilizing part 323 or may exclude both.

Next, the functions of the processing circuitry 44 are described. The processing circuitry 44 includes the mode controlling function 440, the operating function 441, and the sterilizing function 442.

The mode controlling function 440 controls the switching between a photographing mode and a sterilization mode. The photographing mode is used when the subject P is photographed. The sterilization mode is used when the sterilization is performed. For example, the mode controlling function 440 switches between the photographing mode and the sterilization mode in accordance with the operation received by the input interface circuitry 43 of the console 40.

The operating function 441 receives the operation of ordering the execution of the sterilization in the sterilization mode. The operating function 441 also receives the operation of ordering the end of the sterilization. For example, the operating function 441 receives the operation of starting the sterilization through the input interface circuitry 43 of the console 40. That is to say, the console 40 is installed in an operation room different from an inspection room where the gantry 10 is installed, and receives the operation of causing the first sterilizing light source 113 to emit the light capable of sterilization. Thus, the operator, for example a radiologist, can start to sterilize the gantry 10 or the table 30 without entering the inspection room.

The sterilizing function 442 performs the sterilization in the sterilization mode, and when the operating function 441 receives the operation of starting the sterilization. For example, the sterilizing function 442 sterilizes the first flare part 130 by causing the first sterilizing light source 113 to emit light. The sterilizing function 442 sterilizes the operation panel 150 by causing the second sterilizing light source 153 to emit light. The sterilizing function 442 sterilizes the operation button 160 by causing the third sterilizing light source 162 to emit light. The sterilizing function 442 sterilizes the tabletop 33 by causing at least one of the first sterilizing part 322 and the second sterilizing part 323 to emit light.

The first sterilizing light source 113 emits the light capable of sterilization to the opening part 110. For example, the first sterilizing light source 113 emits the light capable of sterilization while the tabletop 33 is inserted into the opening part 110. Thus, since the first sterilizing light source 113 irradiates the tabletop 33 with the light capable of sterilization, the tabletop 33 can be sterilized.

As the distance from the light source to the sterilization object is smaller, the light capable of sterilization has higher illuminance and therefore has the higher sterilizing effect. In view of this, the sterilizing function 442 causes the first sterilizing light source 113 to emit the light capable of sterilization after making the tabletop 33 as close to the first sterilizing light source 113 as possible.

More specifically, the sterilizing function 442 controls the table drive circuitry 32 so that the tabletop 33 is disposed in the opening part 110. That is to say, the table drive circuitry 32 disposes the tabletop 33 at a position set in the opening part 110 in accordance with a part of the tabletop 33 to be sterilized. The table drive circuitry 32 is one example of an activation part. In a case where the sterilization object of the tabletop 33 is an upper surface, the table drive circuitry 32 disposes the tabletop 33 at the highest position in the opening part 110 where the tabletop 33 does not collide with the gantry 10. On the other hand, in a case where the sterilization object of the tabletop 33 is a lower surface, the table drive circuitry 32 disposes the tabletop 33 at the lowest position in the opening part 110 where the tabletop 33 does not collide with the gantry 10. Then, the first sterilizing light source 113 emits the light capable of sterilization while the tabletop 33 is disposed at the position set in the opening part 110.

The opening part 110 has an approximately tubular shape. Therefore, if the table drive circuitry 32 inserts the tabletop 33 into the opening part 110 after raising the tabletop 33 to the upper end of the opening part 110, the tabletop 33 collides with the gantry 10. In view of this, the table drive circuitry 32 raises the tabletop 33 to the upper limit at which the tabletop 33 can be inserted into the opening part 110 without colliding with the gantry 10. Then, the table drive circuitry 32 inserts the tabletop 33 to the opening part 110. In this state, the sterilizing function 442 causes the first sterilizing light source 113 to emit the light capable of sterilization. Thus, the sterilizing function 442 sterilizes the upper surface of the tabletop 33.

On the other hand, in the case of sterilizing the lower surface of the tabletop 33, the sterilizing function 442 inserts the tabletop 33 into the opening part 110 after raising the tabletop 33 to the lower limit at which the tabletop 33 can be inserted into the opening part 110. In this state, the sterilizing function 442 causes the first sterilizing light source 113 to emit the light capable of sterilization. Thus, the sterilizing function 442 sterilizes the lower surface of the tabletop 33. That is to say, the sterilizing function 442 raises the tabletop 33 to the lower limit at which the tabletop 33 can be inserted into the opening part 110 without colliding with the gantry 10. Then, the sterilizing function 442 inserts the tabletop 33 into the opening part 110.

As described above, the X-ray CT apparatus 1 according to the first embodiment includes the gantry 10. The gantry 10 includes the opening part 110 that is the opening formed to have the tubular shape to which the subject P is inserted. The gantry 10 includes the first sterilizing light source 113 that emits the light capable of sterilization, such as ultraviolet rays, to the center of the opening part 110. Thus, the X-ray CT apparatus 1 can reduce the infection risk of people who are involved with the X-ray CT apparatus 1.

First Modification

In the description of the first embodiment, the gantry 10 includes the first sterilizing light source 113 inside the closing cover 112. The gantry 10 may include the first sterilizing light source 113 and a visible light source inside the closing cover 112.

The gantry 10 includes a visible light source that is disposed inside the closing cover 112 and emits the viewable visible light toward the center of the opening part 110. The visible light source is one example of a fifth light source. The visible light source is a light source that emits visible light. For example, the visible light source is a light-emitting diode (LED).

The visible light source is used in the communication with the patient, who is the subject P. For example, the visible light source is used to indicate, to the patient, the period for which the patient is required to hold his breath. The visible light source is used to indicate the photographing period. That is to say, the visible light source emits visible light on the basis of the photographing status of the medical image by the gantry 10.

The subject P who is the patient or the medical worker cannot see the ultraviolet rays. Therefore, the visible light source may be used to indicate the period for which the first sterilizing light source 113 emits the ultraviolet rays corresponding to the light for sterilization. For example, the gantry 10 causes the visible light source to emit visible light while the first sterilizing light source 113 emits ultraviolet rays. Alternatively, the gantry 10 causes the visible light source to blink while the first sterilizing light source 113 emits ultraviolet rays. That is to say, the visible light source emits visible light in accordance with the emission of the light capable of sterilization from the first sterilizing light source 113. Thus, the subject P or the medical worker can recognize the first sterilizing light source 113 emits the ultraviolet rays.

Second Modification

In the description of the first embodiment, the gantry 10 includes the first sterilizing light source 113 inside the closing cover 112 and the first sterilizing light source 113 emits light from 360 degrees along the circumference around the cavity with the tubular shape.

The first sterilizing light source 113 can sterilize the lower side of the tabletop 33 by emitting the light upward from a lower part of the opening part 110. However, the lower side of the tabletop 33 is unlikely to be touched by the subject P. In the case where there is a part that does not need to be sterilized, the first sterilizing light source 113 does not need to emit light from a part of the 360-degree circumference. For example, if the lower side of the tabletop 33 does not need to be sterilized, the first sterilizing light source 113 does not need to deliver light to the range of 90 degrees whose center is the lower end of the opening part 110. In this case, the gantry 10 may exclude the first sterilizing light source 113 in the range where the central angle of the opening part 110 is 90 degrees, in which the center of this range coincides with the lower end of the opening part 110.

Third Modification

In the description of the first embodiment, the first sterilizing part 322, the second sterilizing part 323, the first sterilizing light source 113, the second sterilizing light source 153, and the third sterilizing light source 162 perform the sterilization with ultraviolet rays. However, the first sterilizing part 322, the second sterilizing part 323, the first sterilizing light source 113, the second sterilizing light source 153, and the third sterilizing light source 162 may perform the sterilization by other methods than the ultraviolet rays. For example, each of the first sterilizing part 322, the second sterilizing part 323, the first sterilizing light source 113, the second sterilizing light source 153, and the third sterilizing light source 162 may be a device that performs the sterilization with ultraviolet C (UV-C) light, a device that generates ozone with the ultraviolet light, a device that jets antiseptic solution, an air-conditioning system that is installed in the room where the X-ray CT apparatus 1 is disposed, changes the pressure state of the room, and discharges the air in the room through a duct, or a combination of these. In the case of the air-conditioning system, the air-conditioning system may be used together with the device performing the sterilization by another method. The first sterilizing part 322, the second sterilizing part 323, the first sterilizing light source 113, the second sterilizing light source 153, and the third sterilizing light source 162 perform the sterilization by operating when the subject is not in the room between the photographing times of the X-ray CT apparatus 1. Note that the UV-C light may perform the sterilization when the subject is in the room.

Fourth Modification

Figure 7:
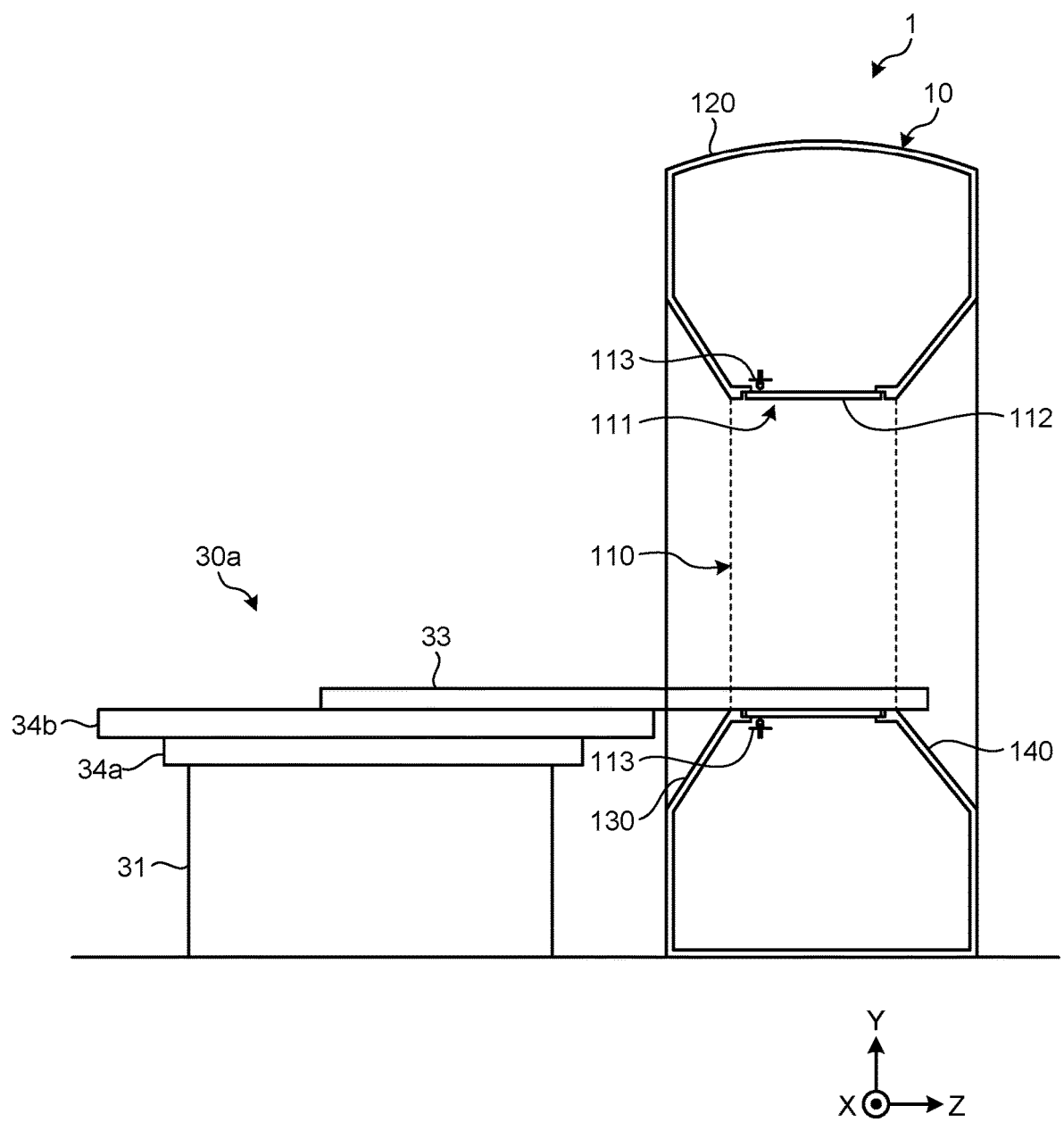
FIG. 7 is a side view illustrating one example of a table according to a fourth modification.

FIG. 7 is a side view illustrating one example of a table 30a according to a fourth modification. The table 30a includes a first supporting part 34a and a second supporting part 34b. The first supporting part 34a and the second supporting part 34b support the tabletop 33 by moving in the longitudinal direction of the tabletop 33 as the tabletop 33 is inserted into the opening part 110. The first supporting part 34a and the second supporting part 34b correspond to one example of a tabletop supporting part. The first supporting part 34a is placed on an upper surface of the base 31. The first supporting part 34a moves in the Z direction by the driving circuitry. The second supporting part 34b is placed on an upper surface of the first supporting part 34a. The second supporting part 34b moves in the Z direction by the driving circuitry. Each of the first supporting part 34a and the second supporting part 34b may be a stick-shaped member such as a frame or a plate-shaped member.

The first supporting part 34a and the second supporting part 34b move in the Z direction when the tabletop 33 is inserted into the opening part 110. Thus, the first supporting part 34a and the second supporting part 34b support the tabletop 33 inserted into the opening part 110. Therefore, the first supporting part 34a and the second supporting part 34b suppress the bending of the tabletop 33 inserted into the opening part 110 due to the weight of the subject P.

The sterilizing function 442 may cause the first sterilizing light source 113 to emit the light capable of sterilization after inserting at least one of the first supporting part 34a and the second supporting part 34b into the opening part 110. Thus, the sterilizing function 442 sterilizes the first supporting part 34a and the second supporting part 34b.

More specifically, the sterilizing function 442 controls the table drive circuitry 32 so as to dispose at least one of the first supporting part 34a and the second supporting part 34b in the opening part 110. That is to say, the table drive circuitry 32 disposes at least one of the first supporting part 34a and the second supporting part 34b at the position set in the opening part 110 in accordance with the part of at least one of the first supporting part 34a and the second supporting part 34b to be sterilized. The first sterilizing light source 113 emits the light capable of sterilization in the state where at least one of the first supporting part 34a and the second supporting part 34b is inserted into the opening part 110 at the position set in the opening part 110.

When a lower surface of the first supporting part 34a is sterilized, the sterilizing function 442 raises the first supporting part 34a to the lower limit at which the first supporting part 34a can be inserted into the opening part 110 without colliding with the gantry 10. Then, the sterilizing function 442 moves the first supporting part 34a toward the opening part 110 as much as possible in the Z direction. That is to say, the sterilizing function 442 moves the first supporting part 34a to the depth side in the opening part 110 as much as possible. Thus, the sterilizing function 442 sterilizes the wider range on the first supporting part 34a.

When a lower surface of the second supporting part 34*b* is sterilized, the sterilizing function 442 raises the second supporting part 34*b* to the lower limit at which the first supporting part 34*a* can be inserted into the opening part 110 without colliding with the gantry 10. Then, the sterilizing function 442 moves the second supporting part 34*b* toward the opening part 110 as much as possible in the Z direction. That is to say, the sterilizing function 442 moves the second supporting part 34*b* to the depth side in the opening part 110 as much as possible. Thus, the sterilizing function 442 sterilizes the wider range on the second supporting part 34*b*.

Note that the sterilizing function 442 may sterilize not just the lower surface of the first supporting part 34*a* or the second supporting part 34*b* but also an upper surface of the first supporting part 34*a* or the second supporting part 34*b*. In this case, the sterilizing function 442 raises the first supporting part 34*a* and the second supporting part 34*b* to the upper limit at which the first supporting part 34*a* and the second supporting part 34*b* do not collide with the gantry 10 and moves the first supporting part 34*a* and the second supporting part 34*b* to the depth side in the opening part 110 as much as possible. Then, the sterilizing function 442 causes the first sterilizing light source 113 to emit the light capable of sterilization, thereby performing the sterilization.

According to at least one embodiment described above, the infection risk of people who are involved with the medical image diagnosis apparatus can be reduced.

While certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. These embodiments and modifications thereof are included in the range and concept of the invention and in the invention according to the scope of claims and the equivalent range thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Regarding the embodiments described above, the following notes are disclosed as aspects and selective features of the invention.

Note 1. A medical image diagnosis apparatus comprising:
- a gantry including a first opening to which a subject is inserted; and
- a first light source configured to emit light capable of sterilization to a center of the first opening.

Note 2. The gantry may include a closing cover configured to cover a second opening provided to a surface in contact with the first opening, and
- the first light source may be provided inside the gantry with respect to the closing cover and face the first opening.

Note 3. The gantry may incorporate an X-ray tube configured to deliver X-rays and an X-ray detector configured to detect the X-rays delivered from the X-ray tube, and
- the first light source may be disposed outside an X-ray passing region from the X-ray tube to the X-ray detector.

Note 4. The gantry may include an operation panel configured to receive touch operation, and
- the operation panel may be configured to release light capable of sterilization.

Note 5. The operation panel may include a panel cover capable of transmitting visible light, and
- the operation panel may be configured to release light capable of sterilization propagating through the panel cover.

Note 6. The gantry may include an operation button configured to receive operation, and
- the operation button may be configured to release light capable of sterilization.

Note 7. The operation button may include a third light source configured to emit light capable of sterilization inside a button cover capable of transmitting visible light.

Note 8. A tabletop on which the subject is placed may be further provided, and
- the tabletop may include a fourth light source configured to emit light capable of sterilization.

Note 9. The fourth light source may be disposed along an edge of the tabletop in a longitudinal direction.

Note 10. The first light source may be disposed inside the closing cover and on a side where a table on which the subject is placed exists.

Note 11. The gantry may exclude the first light source in a range where a central angle of the first opening is 90 degrees, a center of this range coinciding with a lower end of the first opening.

Note 12. The operation panel may include a second light source configured to irradiate the panel cover with the light capable of sterilization inside an exterior cover covering the frame, and
- the operation panel may be configured to release the light capable of sterilization propagating through the panel cover.

Note 13. A fifth light source disposed inside the closing cover and configured to emit viewable visible light to the center of the first opening may be further provided.

Note 14. The fifth light source may be configured to emit visible light, based on a photographing status of a medical image by the frame.

Note 15. The fifth light source may be configured to emit visible light, based on emission of the light capable of sterilization from the first light source.

Note 16. A console installed in an operation room different from an inspection room where the gantry is disposed, and configured to receive operation to cause the first light source to emit the light capable of sterilization may be further provided.

Note 17. The first light source may be configured to emit the light capable of sterilization in a state where the tabletop is inserted in the first opening.

Note 18. A driving circuitry configured to dispose the tabletop at a position set in the first opening in accordance with a part of the tabletop to be sterilized may be further provided, and
- the first light source may be configured to emit the light capable of sterilization in a state where the tabletop is disposed at the position set in the first opening.

Note 19. A tabletop supporting part configured to support the tabletop by moving in a longitudinal direction of the tabletop as the tabletop is inserted in the first opening may be further provided, the driving circuitry may be configured to dispose the tabletop supporting part at a position set in the first opening in accordance with a part of the tabletop supporting part to be sterilized, and the first light source may be configured to emit the light capable of sterilization in a state where the tabletop supporting part is disposed at the position set in the first opening.

What is claimed is:

1. A medical image diagnosis apparatus comprising:
   a gantry including a first opening to which a subject is inserted;
   a first light source configured to emit ultraviolet light to the first opening;
   driving circuitry configured to dispose a tabletop on which the subject is placed at a position set in the first opening, the position having a height that differs between a case where an upper surface of the tabletop is sterilized and a case where a lower surface of the tabletop is sterilized; and
   processing circuitry configured to, when receiving an operation to instruct execution of sterilization, cause the first light source to emit the ultraviolet light in a state where the tabletop is disposed at the position set in the first opening by the driving circuitry.

2. The medical image diagnosis apparatus according to claim 1, wherein
   the gantry includes a closing cover configured to cover a second opening provided to a surface in contact with the first opening, and
   the first light source is provided inside the gantry with respect to the closing cover and faces the first opening.

3. The medical image diagnosis apparatus according to claim 2, further comprising a fifth light source disposed inside the closing cover and configured to emit viewable visible light to a center of the first opening.

4. The medical image diagnosis apparatus according to claim 1, wherein
   the gantry includes an X-ray tube configured to deliver X-rays and an X-ray detector configured to detect the X-rays delivered from the X-ray tube, and
   the first light source is disposed outside an X-ray passing region from the X-ray tube to the X-ray detector.

5. The medical image diagnosis apparatus according to claim 1, wherein
   the gantry includes an operation panel configured to receive touch operation, and
   the operation panel is configured to release ultraviolet light.

6. The medical image diagnosis apparatus according to claim 5, wherein
   the operation panel includes a panel cover capable of transmitting visible light, and
   the operation panel is configured to release ultraviolet light propagating through the panel cover.

7. The medical image diagnosis apparatus according to claim 1, wherein
   the gantry includes an operation button configured to receive operation, and
   the operation button is configured to release ultraviolet light.

8. The medical image diagnosis apparatus according to claim 7, wherein the operation button includes a third light source configured to emit ultraviolet light inside a button cover capable of transmitting visible light.

9. The medical image diagnosis apparatus according to claim 1, further comprising the tabletop, wherein
   the tabletop includes a fourth light source configured to emit ultraviolet light.

10. The medical image diagnosis apparatus according to claim 9, wherein the fourth light source is disposed along an edge of the tabletop in a longitudinal direction.

11. The medical image diagnosis apparatus according to claim 1, further comprising a console installed in an operation room different from an inspection room where the gantry is disposed, and configured to receive operation to cause the first light source to emit the ultraviolet light.

12. The medical image diagnosis apparatus according to claim 1, further comprising a tabletop supporting part configured to support the tabletop by moving in a longitudinal direction of the tabletop as the tabletop is inserted in the first opening, wherein
   the driving circuitry is configured to dispose the tabletop supporting part at a position set in the first opening in accordance with a part of the tabletop supporting part to be sterilized, and
   the first light source is configured to emit the ultraviolet light in a state where the tabletop supporting part is disposed at the position set in the first opening.

* * * * *